(12) United States Patent
Wang et al.

(10) Patent No.: US 7,462,642 B2
(45) Date of Patent: Dec. 9, 2008

(54) ANTI-CANCER COMBINATIONS

(75) Inventors: Liang-Chuan Steve Wang, Auckland (NZ); James William Paxton, Auckland (NZ); Lai-Ming Ching, Auckland (NZ); Bruce Charles Baguley, Auckland (NZ); Philip Kestell, Auckland (NZ)

(73) Assignee: Cancer Research Technology Limited, London (GB)

( * ) Notice: Subject to any disclaimer, the term of this patent is extended or adjusted under 35 U.S.C. 154(b) by 358 days.

(21) Appl. No.: 10/946,833

(22) Filed: Sep. 22, 2004

(65) Prior Publication Data

US 2005/0131059 A1 Jun. 16, 2005

Related U.S. Application Data

(63) Continuation-in-part of application No. PCT/GB03/01320, filed on Mar. 20, 2003.

(51) Int. Cl.
*A61K 31/35* (2006.01)
(52) U.S. Cl. ...................................... 514/455
(58) Field of Classification Search .................. 514/445
See application file for complete search history.

(56) References Cited

U.S. PATENT DOCUMENTS

| | | | |
|---|---|---|---|
| 3,678,077 A | 7/1972 | Nakanishi et al. | |
| 4,602,034 A | 7/1986 | Briet et al. | 514/456 |
| 4,704,355 A | 11/1987 | Bernstein et al. | |
| 5,126,129 A | 6/1992 | Wiltrout et al. | |
| 5,281,620 A | 1/1994 | Denny et al. | |
| 5,464,826 A | 11/1995 | Grindey et al. | |
| 5,620,875 A | 4/1997 | Hoffman et al. | |
| 5,817,684 A | 10/1998 | Fleisch et al. | |
| 5,863,904 A | 1/1999 | Nabel et al. | |
| 5,910,505 A | 6/1999 | Fleisch et al. | |
| 6,174,873 B1 | 1/2001 | Wrenn | |
| 6,194,454 B1 | 2/2001 | Dow | |
| 6,667,337 B2 | 12/2003 | Wilson | |
| 6,806,257 B1 | 10/2004 | Lee et al. | |
| 2001/0041713 A1 | 11/2001 | Waldstreicher et al. | |
| 2003/0003092 A1 | 1/2003 | Krissansen et al. | |

(Continued)

FOREIGN PATENT DOCUMENTS

DE 2015265 A1 10/1970

(Continued)

OTHER PUBLICATIONS

Rustin et al. 5,6-Dimethylxanthenone-4-acetic acid (DMXAA), a novel antivascular agent: phase I clinical and pharmacokinetic study. British Journal of Cancer, 2003, vol. 88, pp. 1160-1167.*

(Continued)

*Primary Examiner*—Ardin Marschel
*Assistant Examiner*—James D Anderson
(74) *Attorney, Agent, or Firm*—Foley & Lardner LLP

(57) ABSTRACT

The present invention relates to synergistic combinations of the compounds of formula I such as compounds of the xanthenone acetic acid class such as 5,6-dimethylxanthenone-4-acetic acid (DMXAA) and NSAIDs, in particular diclofenac, which have anti-tumor activity. More particularly, the invention is concerned with the use of such combinations in the treatment of cancer and pharmaceutical compositions containing said combinations.

6 Claims, 3 Drawing Sheets

U.S. PATENT DOCUMENTS

| | | | |
|---|---|---|---|
| 2004/0087611 | A1 | 5/2004 | Baguley et al. |
| 2004/0204480 | A1 | 10/2004 | Wilson et al. |
| 2006/0009505 | A1 | 1/2006 | Baguley et al. |
| 2007/0060637 | A1 | 3/2007 | Wilson et al. |
| 2007/0082937 | A1 | 4/2007 | Baguley et al. |
| 2008/0070847 | A1 | 3/2008 | Wilson et al. |
| 2008/0070848 | A1 | 3/2008 | Wilson et al. |
| 2008/0070849 | A1 | 3/2008 | Wilson et al. |
| 2008/0070886 | A1 | 3/2008 | Wilson et al. |

FOREIGN PATENT DOCUMENTS

| | | | |
|---|---|---|---|
| DE | 19721211 A1 | | 11/1998 |
| EP | 0278176 A2 | | 8/1988 |
| EP | 0326149 A2 | | 8/1989 |
| EP | 0385467 A1 | | 9/1990 |
| EP | 0488718 A2 | | 6/1992 |
| EP | 0551200 A1 | | 7/1993 |
| EP | 0743064 | | 11/1996 |
| EP | 0584001 B1 | | 5/1997 |
| GB | 0121285.1 | | 9/2001 |
| GB | 0206839.3 | | 5/2002 |
| GB | 0225508.1 | | 11/2002 |
| GB | 0604114.9 | | 3/2006 |
| GB | 0157387.7 | | 8/2006 |
| GB | 0517386.9 | | 8/2006 |
| JP | 09040690 A2 | | 2/1997 |
| JP | 2001247459 | | 9/2001 |
| NZ | 336259 | | 6/1999 |
| NZ | 506060 | | 7/2000 |
| WO | WO 91/04014 | | 4/1991 |
| WO | WO 94/23753 A1 | | 10/1994 |
| WO | WO 95/09621 A1 | | 4/1995 |
| WO | WO 96/32418 A1 | | 10/1996 |
| WO | WO 96/36347 A1 | | 11/1996 |
| WO | WO 97/04761 A1 | | 2/1997 |
| WO | WO 97/34482 A1 | | 9/1997 |
| WO | WO 98/25600 A1 | | 6/1998 |
| WO | WO 98/25615 A1 | | 6/1998 |
| WO | WO 98/25616 A1 | | 6/1998 |
| WO | WO 98/42332 A1 | | 10/1998 |
| WO | WO 98/42334 A1 | | 10/1998 |
| WO | WO 98/42335 A1 | | 10/1998 |
| WO | WO 98/42336 A1 | | 10/1998 |
| WO | WO 98/42337 A1 | | 10/1998 |
| WO | WO 98/42345 A1 | | 10/1998 |
| WO | WO 98/42346 A1 | | 10/1998 |
| WO | WO 98/42650 A2 | | 10/1998 |
| WO | WO 00/10600 A3 | | 3/2000 |
| WO | WO 00/16798 A1 | | 3/2000 |
| WO | WO 00/48591 A1 | | 8/2000 |
| WO | WO 00/76497 | | 12/2000 |
| WO | WO 01/34135 A2 | | 5/2001 |
| WO | WO 01/34137 A2 | | 5/2001 |
| WO | WO 01/34197 A2 | | 5/2001 |
| WO | WO 01/34198 A2 | | 5/2001 |
| WO | WO 02/09700 A1 | | 2/2002 |
| WO | WO03/020259 A2 | | 3/2003 |
| WO | WO 2004/039363 | | 5/2004 |
| WO | WO 2005/027974 A1 | | 3/2005 |
| WO | WO 2007/023302 | | 3/2007 |
| WO | WO 2007/023307 | | 3/2007 |

OTHER PUBLICATIONS

Zhao et al. Improvement of the antitumor activty of intraperitoneally and orally administered 5,6-dimethylxanthenone-4-acetic acid by optimal scheduling. Clinical Cancer Research, 2003, vol. 9, pp. 6545-6550.*

Sausville et al. Contributions of human tumor xenografts to anticancer drug development. Cancer Research, 2006, vol. 66, pp. 3351-3354.*

Johnson et al. Relationships between drug activity in NCI preclinical in vitro and in vivo models and early clinical trials. British J. of Cancer, 2001, 84(10):1424-1431.*

Zhou, et al., "In Vitro and In Vivo Kinetic Interactions of the Antitumour Agent 5, 6-Dimenthylxanthenone-4-Acetic Acid with Thalidomide and Diclofenac", Cancer Chemotherapy and Pharmacology (2001), V. 47, No. 4, pp. 319-326.

Miners, et al., "Preclinical Prediction of Factors Influencing the Elimination of 5, 6-Dimenthylxanthenone-4-Acetic Acid, a New Anticancer Drug", Cancer Research (1997), V. 57, No. 2, pp. 284-289.

Rewcastle, et al., "Potential Antitumor Agents. 61. Structure-Activity Relationships for in Vivo Colon 38 Activity among Disubstituted 9-Oxo-9H-Xanthene-4-Acetic Acids", Journal of Medicinal Chemistry (1991), V. 34, No. 1, pp. 217-222.

Marnett, "Aspirin and Related Nonsteroidal Anti-inflamatory Drugs as Chemopreventive Agents against Colon Cancer", Preventive Medicine (1995), V. 24, No. 2, pp. 103-106.

The International Search Report (PCT/GB03/01320).

Zhou, et al., "Reversible Binding of the Novel Anti-Tumour Agent 5, 6-Dimethylxanthenone-4-Acetic Acid to Plasma Proteins and its Distribution into Blood Cells in Various Species", Journal of Pharmacy and Pharmacology (2001), V. 53, pp. 463-471.

Zhou, et al., "A Difference Between the Rat and Mouse in the Pharmacokinetic Interaction of 5, 6-Dimethylxanthenone-4-Acetic Acid with Thalidomide", Cancer Chemother Pharmacol (2001), V. 47, pp. 541-544.

The Search Report for Application No. GB0206839.3.

Martin, Lawrence J., Ph.D., Aspirin and Related Nonsterodial Anti-inflammatory Drugs as Chemopreventive Agents against Colon Cancer, Preventive Medicine 24, 103-106 (1995).

U.S. Appl. No. 12/064,632, filed Aug. 28, 2006, Green, et al.

U.S. Appl. No. 12/064,633, filed Aug. 25, 2006, Green, et al.

Aitken, et al.; "Synthesis and Antitumour Activity of New Derivatives of Flavone-8-acetic Acid (FAA), Part 4: Variation of the Basic Structure"; Arch. Pharm. Pharm. Med. Chem.; (2000) 333(6) 181-188.

Atwell, et al.; "Potential Antitumor Agents. 60. Relationships between Structure and in Vivo Colon 38 Activity for 5-Substituted 9-Oxoxanthene-4-acetic Acids"; 1990; J. Med. Chem.; 33: 1375-1379.

Atwell, et al.; "Synthesis and anti-tumor activity of topologically-related analogues of flavoneacetic acid"; Anti-Cancer Drug Design; (1989); 4(2) 161-169.

Avastin. Http://www.centerwatch.com/patient/drugs/dru851.html, Jun. 29, 2004.

Baguley, et al.; "Immunomodulatory Actions of Xanthenone Anticancer Agents"; BioDrugs; (1997) 8(2): 119-127.

Baguley, et al.; "Mechanisms of Tumor Blood Flow Inhibition by The Antitumour Drug DMXAA (5,6-dimethylxanthenone-4-acetic acid"; Proceedings of the 11th NCI EORTC AACR Symposium; Copyright © 2000 Stichting NCI-EORTC Symposium on new drugs in cancer therapy; publ. By the AACR; Published as a Supplement to Clinical Cancer Research, vol. 6, Nov. 2000.

Baguley, et al.; "Potential of DMXAA combination therapy for solid tumors"; 2002; Expert Rev. Anticancer Ther.; 2(5): 593-603.

Baguley, et al.; "Serotonin involvement in the antitumour and host effects of flavone-8-acetic acid and 5, 6-dimethylxanthenone-4-acetic acid"; Cancer Chemother. Pharmacol, 33(1), pp. 77-81, 1993.

Baguley, et al.; "Evidence that the 5-hydroxytryptamine antagonist, cyproheptadine, modulates nitric oxide production in mice in response to flavone acetic acid, vinblastine and other agents"; Biol. Nitric Oxide, Proc. Int. Meet.; Meeting Date 1991, vol. 2, (1992); 222-224, 1991.

Baguley, et al.; "Increased Plasma Serotonin Following Treatment With Flavone-8-Acetic Acid, 5,6-Dimethylxanthenone-4-Acetic Acid, Vinblastine, and Colchicine: Relation to Vascular Effects"; Oncology Research; (1997) 9(2), 55-60.

Barefoot, R.; "Speciation of platinum compounds: a review of recent applications in studies of platinum anticancer drugs"; Journal of Chromatography B, 2001, 751:205-211.

Begley, et al.; "The Blood-Brain-Barrier: Principles for Targeting Peptides and Drugs to the Central Nervous System"; J. Pharm. Pharmacol 1996, 48:136-146.

Bibby, et al.; "Flavone acetic acid—from laboratory to clinic and back"; 1993; Anti-Cancer Drugs; 4: 3-17.

Bibby, et al.; "Reduction of Tumor Blood Flow by Flavone Acetic Acid: A Possible Component of Therapy"; 1989; J. Natl. Cancer Inst.; 81:216-220.

Brem, et al; "Interstitial chemotherapy with drug polymer implants for the treatment of recurring gliomas"; J. Neurosurg. 1991, 74:441-446.

Browne, et al.; "Suppression of serum tumour necrosis factor-alpha by thalidomide does not lead to reversal of tumour vascular collapse and anti-tumour activity of 5, 6-dimethylxanthenone-4-acetic acid"; Anticancer Res., 18(6A), pp. 4409-4414, 1998.

Calabresi, et al.; "The Pharmacological Basis of Therapeutics, Ninth Edition," (1996), Goodman & Gilman's The Pharmacological Basis of Therapeutics. Section X, Chemotherapy of Neoplastic Diseases, pp. 1225-1229.

Cao, et al.; "Interferon-inducible Protein 10 Induction and Inhibition of Angiogenesis in Vivo by the Antitumor Agent 5, 6-Dimethylxanthenone-4-acetic Acid (DMXAA)"; Cancer Research; (2001) 61(4), 1517-1521.

Cao, et al.; "Thalidomide increases both intra-tumoural tumour necrosis factor-alpha production and anti-tumour activity in response to 5,6-dimethylxanthenone-4-acetic acid"; Br. J. Cancer, 80(5/6), pp. 716-723, 1999.

Chaplin, et al.; "Antivascular approaches to solid tumor therapy; evaluation of tubulin binding agents"; Proc. Annu. Meet. Am. Assoc. Cancer Res., Mar. 1996, vol. 37, #3009: 440-441 and Abstract.

Ching, et al.; "Antitumour responses to flavone-8-acetic acid and 5, 6-dimethylxanthenone-4-acetic acid in immune deficient mice", Br. J. Cancer; (1992); 66(1), 128-130.

Ching, et al.; "Effect of Tumor Growth on the Macrophage Response to the Antitumour Agent 5,6-Dimethylxanthenone-4-acetic Acid"; Anticancer Research; (1993) 13(6A), 2069-2076.

Ching, et al.; "Haematological effects in mice of the antitumour agents xanthenone-4-acetic acid, 5, 6-dimethylxanthenone-4-acetic acid and flavoneacetic acid"; Cancer Chemother. Pharmacol.; (1991) 28(6), 414-419.

Ching, et al.; "In vitro Methods for Screening Agents with an Indirect Mechanism of Antitumour Activity: Xanthenone Analogues of Flavone Acetic Acid"; Eur. J. Cancer; (1991); 27(12) 1684-1689.

Ching, et al.; "Induction of Natural Killer Activity by Xanthenone Analogues of Flavone Acetic Acid: Relation with Antitumour Activity"; Eur. J. Cancer; (1991); 27(1) 79-83.

Ching, et al.; "Induction of STAT and NF-kappa-B Activation by the Antitumor Agents 5,6-Dimethylxanthenone-4-acetic Acid and Flavone Acetic Acid in a Murine Macrophage Cell Line"; Biochemical Pharmacology; (1999) 58(7) 1173-1181.

Ching, et al.; "Induction of Tumor Necrosis Factor-alpha Messenger RNA in Human and Murine Cells by the Flavone Acetic Acid Analogue 5, 6-Dimethylxanthenone-4-acetic acid"; Cancer Reseach; (1994) 54(4), 870-872.

Ching, et al.; "Stimulation of macrophage tumouricidal activity by 5, 6-dimethylxanthenone-4-acetic acid, a potent analogue of the antitumour agent flavone-8-acetic acid"; Biochemical Pharmacology; (1992) 44(1): 192-195.

Ching, et al.; "Effect of thalidomide on tumour necrosis factor production and anti-tumour activity induced by 5, 6-dimethylxanthenone-4-acetic acid"; Br. J. Cancer, 72(2), pp. 339-343, 1995.

Ching, et al; "Induction of intratumoral tumor necrosis factor (TNF) synthesis and hemorrhagic necrosis by 5, 6-dimethylxanthenone-4-acetic acid (DMXAA) in TNF knockout mice"; Cancer Res., 59(14), pp. 3304-3307, 1999.

Ching, et al.; "Interaction between endotoxin and the antitumour agent 5, 6-dimethylxanthenone-4-acetic acid in the induction of tumor necrosis factor and haemorrhagic necrosis of colon 38 tumors"; Cancer Chemother. Pharmacol., 35(2), pp. 153-160, 1994.

Ching, et al.; "Interaction of thalidomide, phthalimide analogues of thalidomide and pentoxifylline with the antitumour agent 5, 6-dimethylxanthenone-4-acetic acid: concomitant reduction of serum tumour necrosis factor-alpha and enhancement of antitumour activity"; Br. J. Cancer., 78(3), pp. 336-343, 1998.

Ching, et al.; "The Anti-Tumour and Immune-Modulatory Activities of Flavone Acetic and Xanthone Acetic Acids"; 1990; N.P. Das (ed.), flavanoids in Biology and Medicine III. Proceedings of the 3rd International Symposium on Flavonoids in Biology and Medicine; 381-391.

Cliffe, et al.; "Combining bioreductive drugs (SR 4233 or SN 23862) with the vasoactive agents flavone acetic acid or 5, 6-dimethylxanthenone acetic acid"; Int. J. Radiation Oncology Biol. Phys., 29(2), pp. 373-377, 1994.

Coloma, et al.; "Transport across the primate Blood-Brain-Barrier of a genetically engineered Chimeric Monoclonal Antibody to the Human Insulin Receptor"; Pharmaceutical Research 2000, 17(3):266-274.

Combretastatin Update 1: In Ohio Phase 1 Trial, Some Tumors Respond, Patients Experience Vascular Stress; PSA Rising; Medical Pike Briefs; Headline Index: Clinical Trial Phase 1 Results; Nov. 8, 1999.

Corbett, et al.; "Activity of flavone acetic acid (NSC-347512) against solid tumors of mice"; 1986; Investigational New Drugs; 4:207-220.

Djeha, et al.; "Synergistic in vivo antitumor activity in lung and colon cancer xenografts with the vascular disrupting agent DMXAA combined with bevacizumab"; Proc. Am. Assoc. Cancer. Res. Annual Meeting, 2006, 47:55.

Economou, et al.; "Tumour necrosis factor production by IL-2-activated macrophages in vitro and in vivo." Immunology 1989, 67:514-519.

Everett, et al.; "Decarboxylation of the antitumour drugs flavone-8-acetic acid and xanthenone-4-acetic acid by nitrogen dioxide"; Anti-Cancer Drug Design; (1994) 9(1), 68-72.

Everett, et al.; "High-performance ion chromatography applied to free-radical mechanisms in drug design. The problem of ion analysis at high ionic strengths"; Journal of Chromatography A.; (1997) 770(1,2),273-279.

Fujii, et al.; "Vaccination with B7-1 tumor and anti-adhesion therapy with RGD pseudo-peptide (FC-336) efficiently induce anti-metastatic effect"; Clinical & Experimental Metastasis, 16:141-148, 1998.

Futami, et al.; "Cytokine induction and therapeutic synergy with interleukin-2 against murine renal and colon cancers by xanthenone-4-acetic acid derivatives"; J. Immunother., 12(4), pp. 247-255, 1992.

Gamage, et al.; "Structure-activity relationships for substituted 9-oxo-9, 10-dihydroacridine-4-acetic acids: analogues of the colon tumour active agent xanthenone-4-acetic acid"; Anti-Cancer Drug Design; (1992) 7(5), 403-414.

Graham, et al.; Fresh from the Pipeline: Cetuximab; Nature Reviews Drug Discovery 2004, 3:549-550.

Griffioen, et al.; "Angiogenesis Inhibitors Overcome Tumor Induced Endothelial Cell Anergy"; 1999; Int. J. Cancer; 80: 315-319.

Hill, et al.; "Anti-Vascular Approaches to Solid Tumour Therapy: Evaluation of Vinblastine and Flavone Acetic Acid"; Int. J. Cancer; (1995) 63(1), 119-123.

Hornung, et al.; "Augmentation of Natural Killer Activity, Induction of IFN and Development Tumor Immunity During the Successful Treatment of Established Murine Renal Cancer Using Flavone Acetic Acid and IL-2"; The Journal of Immunology (1988), 141(10): 3671-3679.

Jameson, et al.; "Phase I Pharmacokinetic and Pharmacodynamic Study of 5,6-Dimethylxanthenone-4-Acetic Acid (DMXAA), A Novel Antivascular Agent"; 2000; Proc. Am. Soc. Clin Oncol.; 19: 182a.

Joseph, et al.; "Stimulation of Tumors to Synthesize Tumor Necrosis Factor-alpha in Situ Using 5,6-Dimethylxanthenone-4-acetic Acid: A Novel Approach to Cancer Therapy"; Cancer Res. (1999) 59(3), 633-638.

Kanwar, et al.; "Taking lessons from dendritic cells: Multiple xenogeneic ligands for leukocyte integrins have the potential to stimulate anti-tumor immunity"; Gene Therapy, 6: pp. 1835-1844, 1999.

Kanwar, et al.; "Vascular attack by 5, 6-dimethylxanthenone-4-acetic acid combined with B7.1 (CD80)-mediated immunotherapy overcomes immune-resistance and leads to the eradication of large tumors and multiple tumor foci"; Cancer Res., 61(5), pp. 1948-1956,2001.

Kelland, L.; "Targeting Established Tumor Vasculature: A Novel Approach to Cancer Treatment"; Curr.Cancer. Ther. Rev. 2005, 1(1):1-9.

Kestell, et al.; "Determination of xanthenone-4-acetic acid in mouse plasma by high-performance liquid chromatography"; J. of Chromatography; (1991) 564(1), 315-321.

Kestell, et al.; "Disposition of the novel antitumour agent xanthenone-4-acetic acid in the mouse: identification of metabolites and routes of elimination"; Xenobiotica; (1994) 24(7): 635-647.

Kestell, et al.; "Plasma disposition, metabolism and excretion of the experimental antitumour agent 5,6-dimethylxanthenone-4-acetic acid in the mouse, rat and rabbit"; Cancer Chemother. Pharmacol.; (1999) 43(4),323-330.

Kestell, et al.; "Modulation of the pharmacokinetics of the antitumour agent 5,6-dimethylxanthenone-4-acetic acid (DMXAA) in mice by thalidomide"; Cancer Chemother. Pharmacol, 46(2), pp. 135-141, 2000.

Kroll, et al.; "Improving Drug Delivery to Intracerebral Tumor and Surrounding Brain in a Rodent Model: A Comparison of Osmotic versus Bradykinin Modification of the Blood-Brain and/or Blood-Tumor Barriers"; Neurosurgery 1998, 43(4):879-886.

Langer, R.; "New Methods of Drug Delivery". Science 1990, 249:1527-1533.

Lash, et al.; "Enhancement of the anti-tumour effects of the antivascular agent 5,6-dimethylxanthenone-4-acetic acid (DMXAA) by combination with 5-hydroxytryptamine and bioreductive drugs"; Br. J. Cancer, 78(4), pp. 439-445, 1998.

Laws, et al.; "Preclinical in vitro and in vivo activity of 5,6-dimethylxanthenone-4-acetic acid"; British Journal of Cancer; (1995) 71(6), 1204-1209.

Lissoni, et al.; "Neuroimmunotherapy of advanced solid neoplasms with simple evening subcutaneous injection of low-dose interleukin-2 and melatonin: Preliminary results" European Journal of Cancer (1993) vol. 29A(2), pp. 185-189.

Maier, et al.; "In-Vitro inhibition of endothelial cell growth by the antiangiogenic drug AGM-1470 (TNP-470) and the anti-endoglin antibody TEC-11." Anti-Cancer Drugs 1997; 8: 238-244.

Marona, H.; "Synthesis and Properties of Some Xanthone-2-Alkylcarboxylic acids and Xanthone-2-Glyoxal." Polish Journal of Chemistry, 54:2059 (1980).

McKeage, et al.; "Plasma pharmacokinetics of the antitumour agents 5,6-dimethylxanthenone-4-acetic acid, xanthenone-4-acetic acid and flavone-8-acetic acid in mice"; Cancer Chemother. Pharmacol.; (1991) 28(6), 409-413.

McLachlan, et al.; "The Potential of Cyclosporin A as an Anti-Tumour Agent"; Int. J. Immun., 1990, V. 12 (5), p. 469-479.

Moilanen, et al.; "Persistent induction of nitric oxide synthase in tumours from mice treated with the anti-tumour agent 5,6-dimethylxanthenone-4-acetic acid"; British Journal of Cancer; (1998) 77(3): 426-433.

Murata, et al.; "Comparative effects of combretastatin A-4 disodium phosphate and 5,6-dimethylxanthenone-4-acetic acid on blood perfusion in a murine tumour and normal tissues"; Int. J. Radiat. Biol; (2001) vol. 77, No. 2, 195-204.

Nakamura et al.; "Antitumor Effect of Recombinant Human Interleukin 1 Alpha against Murine Syngeneic Tumors"; Jpn. J. Cancer Research (Gann) 1986; 77: 767-773.

Nakanishi, et al.; "Carboxylic Acids". Chem. Abstr. 76:126784w (1972), (Abstract of Japan A-7,200,425).

Nakanishi, et al.; "Studies of Anti-Inflammatory Agents XXXI; Studies on the Synthesis and Anti-Inflammatory Activity of Xanthenyl- and Benzo-pyranopyridinylacetic acid Derivatives." Yakugaku Zasshi, 96:99-109 (1976).

Nawrocki et al.; "Genetically modified tumour vaccines-where we are today"; Cancer Treatment Reviews, (1999), vol. 25, pp. 29-46.

Neuwelt, et al.; "Increased Delivery of Tumor-specific Monoclonal Antibodies to Brain after Osmotic Blood-Brain-Barrier modification in Patients with Melanoma Metastatic to the Central Nervous System"; Neurosurgery 1987, 20(6):885-895.

Nishino, et al.; "Oxidation of 9-Xanthenones with Lead (IV) Acetate. Formation of Di-gamma-lactones." Bull. Chem Soc. Jpn. 56:2847-48 (1983).

Nishino, et al.; "Regioselective Carboxylation of 9-Xanthenones with Manganese (III) Acetate." Bull. Chem Soc. Jpn. 56:474-480 (1983).

O'Reilly, et al.; "Endostatin: An Endogenous Inhibitor of Angiogenesis and Tumor Growth"; 1997; Cell; 88: 277-285.

Pang, et al.; "Antitumour Activity of the Novel Immune Modulator 5, 6-Dimethylxanthenone-4-acetic Acid (DMXAA) in Mice Lacking the Interferon-gamma Receptor"; European Journal of Cancer; (1998) 34(8): 1282-1289.

Patel, et al.; "The Effect of 5, 6-Dimethylxanthenone-4-acetic acid on Tumour Necrosis Factor Production by Human Immune Cells"; Anticancer Research (1997) 17(1A), 141-150.

Peckham, et al.; "Oxford Textbook of Oncology". Oxford University Press, vol. 1. p. 451, 1995.

Pedley, et al.; "Ablation of Colorectal Xenografts with Combined Radioimmunotherapy and Tumor Blood Flow-modifying Agents"; Cancer Research; (1996) 56(14), 3293-3300.

Pedley, et al.; "Enhancement of Radioimmunotherapy by Drugs Modifying Tumour Blood Flow in a Colonic Xenograft Model"; Int. J. Cancer; (1994) 57(6),830-835.

Pedley, et al.; "Enhancement of antibody-directed enzyme prodrug therapy in colorectal xenografts by an antivascular agent"; Cancer Res., 59(16), pp. 3998-4003, Aug. 15, 1999.

Perera, et al.; "Activation of LPS-Inducible Genes by the Antitumor Agent 5,6-Dimethylxanthenone-4-Acetic Acid in Primary Murine Macrophages"; The Journal of Immunology; (1994) 153(10),4684-4693.

Phillips, R.M.; "Inhibition of DT-diaphorase (NAD(P)H: quinone oxidoreductase, EC 1.6.99.2) by 5,6-dimethylxanthenone-4-acetic acid (DMXAA) and flavone-8-acetic acid (FAA): Implications for bioreductive drug development"; Biochem. Pharmacol., 58(2), pp. 303-310, 1999.

Philpott, et al.; "Induction of tumor necrosis factor-alpha by single and repeated doses of the antitumour agent 5, 6-dimethylxanthenone-4-acetic acid"; Cancer Chemother. Pharmacol.; (1995) 36(2) 143-148.

Philpott, et al.; "Production of tumour necrosis factor-alpha by cultured human peripheral blood leukocytes in response to the antitumour agent 5, 6-dimethylxanthenone-4-acetic acid (NSC 640488)"; British Journal of Cancer; (1997) 76(12): 1586-1591.

Plowman, et al.; "Flavone Acetic Acid: A Novel Agent with Preclinical Antitumor Activity Against Colon Adenocarcinoma 38 in Mice"; 1986; Cancer Treatment Reports; 70(50): 631-635.

Pruijn, et al.; "Mechanisms of enhancement of the antitumour activity of melphalan by the tumour-blood-flow inhibitor 5, 6-dimethylxanthenone-4-acetic acid"; Cancer Chemother. Pharmacol., 39(6), pp. 541-546, 1997.

PTCL. Chemical and Other Safety Information. "ptcl.chem.ox.ac.uk/MSDS".

Rewcastle, et al.; "Light-Induced Breakdown of Flavoneacetic Acid and Xanthenone Analogues in Solution"; J. Natl. Cancer Inst.; (1990); 82(6): 528-529.

Rewcastle, et al.; "Potential Antitumor Agents. 58. Synthesis and Structure-Activity Relationships of Substituted Xanthenone-4-acetic Acids Active against the Colon 38 Tumor in Vivo"; J. Med. Chem. 32(4), pp. 793-799, 1989.

Rewcastle, et al.; "Potential Antitumor Agents. 62. Structure-Activity Relationships for Tricyclic Compounds Related to the Colon Tumor Active Drug 9-Oxo-9H-xanthene-4-acetic Acid"; 1991: J. Med. Chem.; 34: 491-496.

Rewcastle, et al.; "Potential Antitumour Agents. 63. Structure-Activity Relationships for Side-Chain Analogues of the Colon 38 Active Agent 9-oxo-9H-xanthene-4-acetic Acid"; J. Med. Chem.; (1991) 34(9), 2864-2870.

Rewcastle, G. W.; "Synthesis and Development of Two New Classes of Anticancer Drugs: the tricyclic Carboxamides and the xanthenoneacetic acids"; Chemistry in New Zealand; (1989); 53(6): 145-150.

Rieckmann, et al.; "Okadaic Acid is a potent inducer of AP-1, NF-kappa-B, and Tumor-Necrosis Factor-alpha in Human B Lymphocytes." Biochem. Biophys. Res. Commun. 1992; 187(1): 51-57.

Rustin, et al.; "Impact on Tumour Perfusion Measured by Dynamic Magnetic Resonance Imaging (MRI), in the Phase 1 Trial of 5,6-dimethylxanthenone-4-aceticAcid (DMXAA)"; Proc. 10th NCI-EORTC Symp. New Drugs; 1998; 10: 126.

Rustin, G.; "Vascular Targeting in the Clinic"; Abstract; ICTR 2000: 1st Int'l Conference on Translational Research A., 2000.

Saltiel, E.; "Erlotinib". Http://www.medicinenet.com/erlotinib/article.htm. Nov. 28, 2004.

Saltiel, E.; "Gefitinib". Http://www.medicinenet.com/gefitinib/article.htm. Jun. 22, 2005.

Shoemaker, et al.; "Pleiotropic Resistance and Drug Development"; 1986; Cancer Drug Resistance; 143-149.

Showalter, H.; "Potential Antitumor Agents. 61. Structure-Activity Relationships for In Vivo Colon 38 Activity Among Disubstituted 9-Oxo-9H-xanthene-4-acetic acids"; 1991; Chemtracts: Org. Chem. 4(2): 168-171. Commentary of Rewcastle: J. Med. Chem. 1991, 34:217.

Siemann, et al.; "Enhanced Antitumor Efficacy through the combination of Vascular Targeting Agents and Conventional Anticancer Drugs". Proceedings of the American Association for Cancer Research, 2000, vol. 41, p. 525.

Siemann, et al.; "Vascular Targeting Agents Enhanced Chemotherapeutic Agent Activities in Solid Tumor Therapy", Int. J. Cancer: 99, 1-6 (2002).

SIIM, et al.; Marked potentiation of the antitumour activity of chemotherapeutic drugs by the antivascular agent 5,6-dimethylxanthenone-4-acetic acid (DMXAA); 2003; Cancer Chemother Pharmacol; 51: 43-52.

SIIM, et al.; "Nitro Reduction as an Electronic Switch for Bioreductive Drug Activation"; Oncology Research; (1997) 9(6/7), 357-369.

SIIM, et al.; "Scintigraphic Imaging of the Hypoxia Marker 99m-Technetium-labeled 2,2'-(1,4-Diaminobutane)bis(2-methyl-3-butanone) Dioxime (99mTc-labeled HL-91; Prognox): Noninvasive Detection of Tumor Response to the Antivascular Agent 5, 6-Dimethylxanthenone-4-acetic Acid"; Cancer Research; (2000) 60(16), 4582-4588.

Simone, et al.; "Oncology". Cecil Text Book of Medicine. 20th Edition vol. 1, W. B. Saunders Company. 1997, p. 1004-1010.

Temsamani, et al.; "Brain drug delivery technologies: novel approaches for transporting therapeutics"; Pharm. Sci. Technology Today 1998, 3(5):155-162.

Thomsen, et al.; "Evidence for the Production of Nitric Oxide by Activated Macrophages Treated with the Antitumor Agents Flavone-8-acetic Acid and Xanthenone-4-acetic Acid"; Cancer Research; (1990); 50(21),6966-6970.

Thomsen, et al.; "Modulation of superoxide production from murine macrophages by the antitumour agent flavone acetic acid and xanthenone acetic acid analogues"; Biochemical Pharmacology; (1992) 43(2): 386-389.

Thomsen, et al.; "Nitric Oxide: its production in host-cell-infiltrated EMT6 spheroids and its role in tumor cell killing by flavone-8-acetic acid and 5, 6-dimethylxanthenone-4-acetic acid"; Cancer Chemother. Pharmacol. (1992) 31(2), 151-155.

Thomsen, et al.; "Nitric Oxide Production in endotoxin-resistant C3H/HeJ mice stimulated with flavone-8-acetic acid and xanthenone-4-acetic acid analogues"; Biochem. Pharmacol, 43(11); pp. 2401-2406; 1992.

Thomsen, et al.; "Tumor-dependent increased plasma nitrate concentrations as an indication of the antitumor effect of flavone-8-acetic acid and analogues in mice"; Cancer Res., 51 (1), pp. 77-81, 1991.

Thrash-Bingham, et al.; "aHIF: A natural antisense transcript overexpressed in human renal cancer during hypoxia"; The Journal of the National Cancer Institute, (1999), vol. 91(2), pp. 143-151.

Tyle, P.; "Iontophoretic Devices for Drug Delivery"; Pharmaceutical Research 1986, 3(6):318-326.

Van Der Auwera, et al.; "Conformational Features of Four Model Tripeptides Having Piv-Pro-MeXaa-NMe2 Sequences"; Bull. Soc. Chim. Belg.; (1988) 97(3): 199-207.

Van Moorsel, et al.; "Combination Chemotherapy Studies with Gemcitabine and Etoposide in Non-Small Cell Lung and Ovarian Cancer Cell Lines." Biochemical Pharmacology, 1999, vol. 57, pp. 407-415.

Veszelovszky, et al.; "Flavone Acetic Acid and 5, 6-Dimethylxanthenone-4-acetic Acid: Relationship between Plasma Nitrate Elevation and the Induction of Tumour Necrosis"; Eur. J. Cancer, Part A; (1993) 29A(3): 404-408.

Vincent, et al.; "Chemotherapy with DMXAA (5, 6-dimethylxanthenone-4-acetic acid) in combination with CI-1010 (1H-imidazole-1-ethanol, alpha-[[(2-bromoethyl)amino]methyl]-2-nitro-, mono-hydrobromide (Risomer)) against advanced stage murine colon carcinoma 26"; Oncology Reports; (1997) 4(1), 143-147.

Watts, et al.; "Changes in coagulation and permeability properties of human endothelial cells in vitro induced by TNF-alpha or 5,6 MeXAA"; British Journal of Cancer, Suppl.; (1996) 74(27): SI64-S167.

Webster, et al.; "Metabolism and Elimination of 5,6-Dimethylxanthenone-4-Acetic Acid in the Isolated Perfused Rat Liver"; Drug Metabolism and Disposition (1995) 23(3): 363-368.

Westland, et al.; "Activated non-neural specific T cells open the blood-brain-barrier to circulating antibodies"; Brain 1999, 122:1283-1291.

Wiesenthal. "Is one 'sensitive' drug better than another? Can you detect drug synergy? What are the best drug combinations?" http://weisenthal.org/feedback.html, Feb. 4, 2002.

Wilkinson, et al.; "Tamoxifen (Noivadex) Therapy—Radionale for Loading Dose Followed by Maintenance Dose for Patients with Metastatic Breast Cancer." Cancer Chemotherapy Pharmacol. (1982) 10, 33-35.

Wilson, et al.; "Combination of the Antivascular Agent DMXAA with Radiation and Chemotherapy", International Journal of Oncology, Biology and Physics, vol. 46, No. 3, Feb. 1, 2000, abstract 46, p. 706.

Wilson, et al.; "Enhancement of Tumor Radiation Response by the Antivascular Agent 5,6-Dimethylxanthenone-4-Acetic Acid"; Int. J. Radiation Oncology Biol. Phys.; (1998) vol. 42 No. 4, 905-908.

Wilson, et al.; "Tertiary amine N-oxides as bioreductive drugs: DACA N-oxide, nitracrine N-oxide and AQ4N"; British Journal of Cancer Supplemental; (1996) 74(27), S43-S47.

Wilson, et al.; "Hypoxia-Activated Prodrugs as Antitumour Agents: Strategies for Maximizing Tumor Cell Killing"; Clinical and Experimental Pharmacology and Physiology; (1995) 22(11), 881-885.

Wouters, et al.; "Hypoxia as a target for combined modality treatments"; 2002; European J. of Cancer; 38: 240-257.

Zaharko, et al.; Therapeutic and Pharmacokinetic Relationships of Flavone Acetic Acid: An Agent with Activity Against Solid Tumors; 1986; Cancer Treatment Reports; 70(12): 1415-1421.

Zaks-Zilberman, et al.; "Induction of Adrenomedullin mRNA and Protein by Lipopolysaccharide and Paclitaxel (Taxol) in Murine Macrophages"; Infection and Immunity; (1998) 66 (10), 4669-4675.

Zhang, et al.; "Conjugation of brain-derived neurotrophic factor to a blood-brain-barrier resistant drug targeting system enables neuroprotection in reginal brain ischemia following intravenous injection of the neurotrophin."; Brain Research 2001, 889:49-56.

Zhao, et al.; "Effects of the serotonin receptor antagonist cyproheptadine on the activity and pharmacokinetics of 5, 6-dimethylxanthenone-4-acetic acid (DMXAA)"; Cancer Chemother. Pharmacol, 47(6), pp. 491-497,2001.

Zhao, et al.; Oral activity and pharmacokinetics of 5,6-dimethylxanthenone acetic acid (DMXAA) in mice, Cancer Chemother. Pharmacol. (2002), 49, 20-26.

Zhou, et al.; "5,6-dimethylxanthenone-4-acetic acid (DMXAA): a new biological response modifier for cancer therapy"; Invest New Drugs. Aug 2002;20(3):281-95.

Zhou, et al.; "Determination of the covalent adducts of the novel anti-cancer agent 5, 6-dimethylxanthenone-4-acetic acid in biological samples by high-permormance liquid chromatography"; J. of Chromatography B; (2001) 757: 343-348.

Zhou, et al.; "Determination of unbound concentration of the novel anti-tumour agent 5,6-dimethylxanthenone-4-acetic acid in human plasma by ultrafiltration followed by high-performance liquid chromatography with fluorimetric detection"; J. of Chromatography B; (2001) 757(2),359-363.

Zhou, et al.; "Effects of anticancer drugs on the metabolism of the anticancer drug 5,6-dimethylxanthenone-4-acetic (DMXAA) by human liver microsomes"; 2001; J. Clin. Pharmacol.; 52: 129-136.

Zhou, et al.; "Determination of two major metabolites of the novel anti-tumor agent 5, 6-dimethylxanthenone-4-acetic acid in hepatic microsomal incubations by high-performance liquid chromatography with fluorescence detection"; J. of Chromatography B; (1999) 734(1): 129-136.

Zhou, et al.; "Identification of the Human Liver Cytochrome P450 Isoenzyme Responsible for the 6-Methylhydroxylation of the Novel Anticancer Drug 5, 6-Dimethylxanthenone-4-Acetic Acid"; Drug Metabolism and Disposition (2000) 28(12) 1449-1456.

Zitvogel, et al.; "Interleukin-12 and B7.1 co-stimulation cooperate in the induction of effective antitumor immunity and therapy of established tumors"; Eur. J. Immunol, (1996), vol. 26, pp. 1335-1341.

ZWI, et al.; "Blood Flow Failures as a Major Determinant in the Antitumor Action of Flavone Acetic Acid"; 1989; J. Natl. Cancer Inst.; 81: 1005-1013.

ZWI, et al.; "Necrosis in non-tumour tissues caused by flavone acetic acid and 5,6-dimethyl xanthenone acetic acid"; Br. J. Cancer; (1990) 62(6), 932-934.

ZWI, et al.; "The Morphological Effects of the Anti-Tumor Agents Flavone Acetic Acid and 5,6-Dimethyl Xanthenone Acetic Acid on the Colon 38 Mouse Tumor"; Pathology; (1994) 26(2), 161-169.

ZWI, et al.; "Correlation between immune and vascular activities of xanthenone acetic acid antitumor agents"; Oncol. Res., 6(2), pp. 79-85, 1994.

* cited by examiner

ANTI-CANCER COMBINATIONS

This application is a Continuation-In-Part of PCT/GB03/01320, filed Mar. 20, 2003, which published in English and designated the U.S., and which claimed the priority of Great Britain patent application No. GB 0206839.3, filed Mar. 22, 2002, the entirety of each of which is hereby incorporated by reference.

The present invention relates to synergistic combinations of the compounds of the class having the formula (I) as defined below, for example compounds of the xanthenone acetic acid class having the formula (II) as defined below, such as 5,6-dimethylxanthenone-4-acetic acid (DMXAA) and non-steroidal anti-inflammatory drugs such as cyclooxygenase inhibitors, in particular diclofenac, which have anti-tumour activity. More particularly, the invention is concerned with the use of such combinations in the treatment of cancer and pharmaceutical compositions containing such combinations.

5,6-dimethylxanthenone-4-acetic acid (DMXAA) is represented by the following formula:

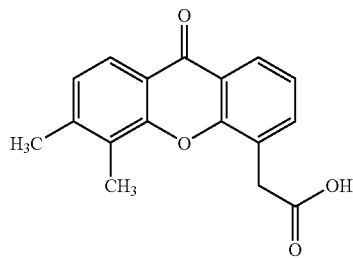

Phase I clinical trials of DMXAA have recently been completed, with dynamic MRI showing that it induces a significant reduction in tumour blood flow at well-tolerated doses. DMXAA is thus one of the first antivascular agents for which activity (irreversible inhibition of tumour blood flow) has been documented in human tumours. These findings are in agreement with preclinical studies using tumours or human tumour xenografts which showed that its antivascular activity produced prolonged inhibition of tumour blood flow leading to extensive regions of haemorrhagic necrosis.

Non-steroidal anti-inflammatory drugs (NSAIDs) share the capacity to suppress the signs and symptoms of inflammation. Many also exert antipyretic and analgesic effects. Salicylate is the major anti-inflammatory metabolite of aspirin, the original NSAID. Aspirin irreversibly acetylates and blocks platelet cyclooxygenase. Other NSAIDS are reversible inhibitors. Selectivity for COX-1 and COX-2 is variable for many of the traditional NSAIDs. Ibuprofen inhibits COX-2 and COX-1 to approximately the same extent. However, highly selective COX-2 inhibitors (celecoxib and rofecoxib) are now available.

Diclofenac is a non-steroidal anti-inflammatory drug (NSAID) having the chemical name 2-[(2,6-dichlorophenyl)amino]benzeneacetic acid. Diclofenac potassium is available as Cataflam® with Diclofenac sodium available as VOLTAREN®. Diclofenac is indicated for the acute and chronic treatment of signs and symptoms of osteoarthritis and rheumatoid arthritis and treatment of ankylosing spondylitis, analgesia and primary dysmennorrhea.

Pharmacokinetic drug interaction is defined as one where drug A affects the plasma (or tissue) concentration of drug B, by altering the latter's absorption, distribution, excretion or metabolism (Dorr and Fritz, *Cancer Chemotherapy Handbook*, Henry Kimpton Publishers, London. 1980; Tenenbaum, L., Cancer chemotherapy—a Reference Guide, W. B. Saunders, New York. 1989). The combination therapy of 5,6-dimethylxanthenone-4-acetic acid (DMXAA) and thalidomide is one of the examples of pharmacokinetic interactions that involve alteration in drug metabolism.

UGT 1A9, UGT 2B7, and CYP 1A2 have been shown to be involved in the metabolism of DMXAA (Miners et al Cancer Res., 57: 284-289, 1997; Zhou et al J. Chromatog. B, 757: 343-348, 2001). Glucuronidation is the major metabolic elimination pathway of DMXAA (Miners et al Cancer Res., 57: 284-289, 1997; Kestell et al, Cancer Chemother. Pharmacol., 46: 135-141, 2000). DMXAA can also be metabolized by 6-methylhydroxylation, but to a lesser extent (Zhou et al J. Chromatog. B, 757: 343-348, 2001). The product of glucuronidation, DMXAA acyl glucuronide (DMXAA-G), and the product of 6-methylhydroxylation, 6-methylhydroxyl-5-methylxanthenone-4-acetic acid (6-OH— MXAA), are then excreted in bile and urine (Zhou et al J. Chromatog. B, 757: 343-348, 2001).

Diclofenac has been shown to affect the metabolism of DMXAA. At a concentration of 100 μM, diclofenac has been shown to significantly inhibit glucoronidation (>70%) and 6-methylhydroxylation (>54%) of DMXAA in mouse and human microsomes. In vivo, diclofenac (100 mg/kg i.p.) has been shown to result in a 24% and 31% increase in the plasma DMXAA AUC (area under the plasma concentration-time curve) and a threefold increase in $T_{1/2}$ ($P<0.05$) in male and female mice respectively (Zhou et al (2001) Cancer Chemother Pharmacol 47 319-326).

It has now surprisingly been found that by administering, either concomitantly or sequentially, compounds having the formula (I) as defined below with an NSAID such as the NSAID diclofenac at NSAID concentrations which do not affect the plasma pharmacokinetics of compounds of formula (I), potentiation of the antitumour activity of compounds formula (I) as defined above is nevertheless achieved.

In particular co-administration of compounds of formula (I) as defined below such as DMXAA with NSAIDS such as diclofenac provides a therapeutic gain against sub-cutaneously established (3-5 mm, approximately 20 mg) colon 38 tumour fragments at concentrations of NSAID which does not significantly affect the plasma pharmacokinetics of the compound of formula (I) as defined below.

Thus, in a first aspect, the present invention provides a method for modulating neoplastic growth, which comprises administering to a mammal, including a human, in need of treatment an effective amount of a compound of the formula (I):

Formula (I)

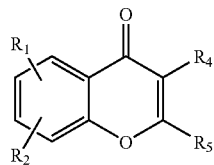

or a pharmaceutically acceptable salt or ester thereof and concomitantly or sequentially administering an effective amount of a NSAID, wherein said effective amount of said NSAID is less than that required to substantially alter the plasma pharmacokinetics of the compound of the xanthenone acetic acid class having the formula (I) as defined above in said mammal;

wherein:

(a) $R_4$ and $R_5$ together with the carbon atoms to which they are joined, form a 6-membered aromatic ring having a substituent —$R_3$ and a radical —(B)—COOH where B is a linear or branched substituted or unsubstituted $C_1$-$C_6$ alkyl radical, which is saturated or ethylenically unsaturated, and wherein $R_1$, $R_2$ and $R_3$ are each independently selected from the group consisting of H, $C_1$-$C_6$ alkyl, halogen, $CF_3$, CN, $NO_2$, $NH_2$, OH, OR, NHCOR, $NHSO_2R$, SR, $SO_2R$ or NHR, wherein each R is independently $C_1$-$C_6$ alkyl optionally substituted with one or more substituents selected from hydroxy, amino and methoxy; or (b) one of $R_4$ and $R_5$ is H or a phenyl radical, and the other of $R_4$ and $R_5$ is H or a phenyl radical which may optionally be substituted, thenyl, furyl, naphthyl, a $C_1$-$C_6$ alkyl, cycloalkyl, or aralkyl radical; $R_1$ is H or a $C_1$-$C_6$ alkyl or $C_1$-$C_6$ alkoxy radical; $R_2$ is the radical —(B)—COOH where B is a linear or branched substituted or unsubstituted $C_1$-$C_6$ alkyl radical, which is saturated or ethylenically unsaturated.

Where the radical —(B)—COOH is a substituted $C_1$-$C_6$ alkyl radical, the substituents may be alkyl, for example methyl, ethyl, propyl or isopropyl, or halide such as fluoro, chloro or bromo groups. A particularly preferred substituent is methyl.

In one embodiment of the first aspect of the invention, the compound of the formula (I) as defined above is a compound of the formula (II),

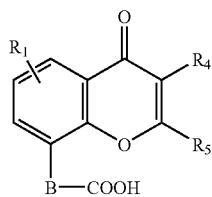

Formula (II)

where $R_1$, $R_4$, $R_5$ and B are as defined above for formula (I) in part (b).

In a preferred embodiment of the first aspect of the invention, the compound of formula (I) as defined above is a compound of the formula (III)

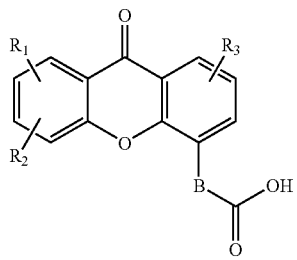

Formula (III)

wherein $R_1$, $R_2$ and $R_3$ are each independently selected from the group consisting of H, $C_1$-$C_6$ alkyl, halogen, $CF_3$, CN, $NO_2$, $NH_2$, OH, OR, NHCOR, $NHSO_2R$, SR, $SO_2R$ or NHR, wherein each R is independently $C_1$-$C_6$ alkyl optionally substituted with one or more substituents selected from hydroxy, amino and methoxy;

wherein B is as defined for formula (I) above;

and wherein in each of the carbocyclic aromatic rings in formula (I), up to two of the methine (—CH═) groups may be replaced by an aza (—N═) group;

and wherein any two of $R_1$, $R_2$ and $R_3$ may additionally together represent the group —CH═CH—CH═CH—, such that this group, together with the carbon or nitrogen atoms to which it is attached, forms a fused 6 membered aromatic ring.

Preferably, the compound of formula (III) is a compound of the formula (IV):

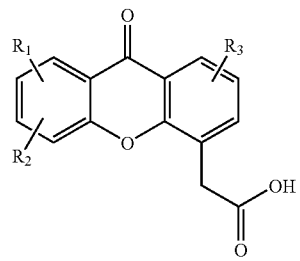

Formula (IV)

wherein R, $R_1$, $R_2$ and $R_3$ are as defined for formula (III).

In a preferred embodiment of the compound of formula (IV), $R_2$ is H, one of $R_1$ and $R_3$ is selected from the group consisting of $C_1$-$C_6$ alkyl, halogen, $CF_3$, CN, $NO_2$, $NH_2$, OH, OR, NHCOR, $NHSO_2R$, SR, $SO_2R$ or NHR, wherein each R is independently $C_1$-$C_6$ alkyl optionally substituted with one or more substituents selected from hydroxy, amino and methoxy, and the other of $R_1$ and $R_3$ is H.

Preferably, the compound of formula (IV) is of the formula (V):

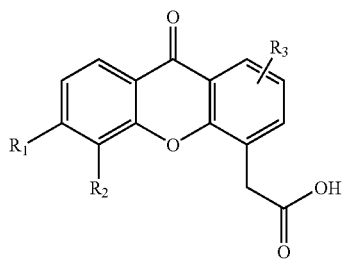

Formula (V)

wherein R, $R_1$, $R_2$ and $R_3$ are as defined for formula IV.

Most preferably, the compound of formula (IV) is 5,6-dimethylxanthenone 4 acetic acid (DMXAA).

In the context of the present invention, a concentration of NSAID is considered not to substantially alter the plasma pharmacokinetics of the compound of formula (I) as defined above in the mammal if the plasma concentration of the compound of formula (I) in the mammal is not significantly increased (P<0.05), as judged by the compound of formula (I) AUC (area under the plasma concentration-time curve) and/or $T_{1/2}$ of the compound of formula (I) in plasma. Preferably neither the AUC nor the $T_{1/2}$ values are significantly different between mammals treated with the compound of formula (I) monotherapy and those treated with the compound of formula (I) and the NSAID. An alternative or preferably additional test to assess whether or not a concentration of NSAID may be considered in the context of the present invention to not substantially alter the plasma pharmacokinetics of a compound of formula (I) in a mammal may be measurement of metabolites. For example, where the compound of formula (I) is DMXAA, concentration of metabolites such as DMXAA acyl glucoronide (DMXAA-G) and 6-methylhydroxyl-5-methylxanthenone-4-acetic acid (6-OH-MXAA) may be measured. A concentration of NSAID may be considered to not substantially alter the plasma pharmacokinetics of DMXAA in a mammal if the NSAID does not cause significant inhibition of glucoronidation or 6-methylhydroxylation of DMXAA as assessed by measurement of DMXAA-G or 6-OH-MXAA concentration in an assay of DMXAA metabolism in the presence and absence of the NSAID. Suitable in vitro and in vivo assays are known to the skilled person. For example, an in vitro assay based on liver microsomal preparations which may be used to assess DMXAA metabolism is described in Zhou et al (2001) Cancer Chemother Pharmacol 47 319-326. More suitably, an High Performance Liquid Chromatography (HPLC) based method may be used to measure suitable HPLC based assay may be used to measure the concentrations of NSAID metabolites in the plasma or urine of a subject. Such an assay is described in Kestell, P et al (1999): Cancer Chemother. Pharmacol. 43, 323-330, the contents of which is hereby incorporated by reference.

In another aspect, the present invention provides the use of a compound of formula (I) as defined above or a pharmaceutically acceptable salt or ester thereof for the manufacture of a medicament, for administration either concomitantly or sequentially with a unit dose of a cyclooxygenase inhibitor compound, for the modulation of neoplastic growth, wherein said unit dose comprises said NSAID compound in an amount which is less than that required to substantially alter the plasma pharmacokinetics of the compound of formula (I) in the mammal.

In a further aspect, the present invention provides the use of a NSAID compound for the manufacture of a unit dose of a medicament, for simultaneous, separate or sequential administration with a compound of formula (I) as defined above or a pharmaceutically acceptable salt or ester thereof, for the modulation of neoplastic growth, wherein said unit dose comprises said NSAID compound in an amount which is less than that required to substantially alter the plasma pharmacokinetics of DMXAA in a subject to be treated.

In a still further aspect, the present invention provides a combined preparation of a compound of formula (I) as defined above or a pharmaceutically acceptable salt or ester thereof and a NSAID compound for simultaneous, separate or sequential use, e.g. for modulation of neoplastic growth, wherein the compound of formula (I) or pharmaceutically acceptable salt or ester thereof and the NSAID compound are present in a potentiating ratio, and wherein said NSAID compound is present in an amount which is less than that required to substantially alter the plasma pharmacokinetics of the compound of formula (I) in a subject to which the combination is administered.

In a further aspect, there is provided a pharmaceutical formulation comprising a combination of a compound of formula (I) as defined above or a pharmaceutically acceptable salt or ester thereof and a NSAID compound wherein a unit dose of said pharmaceutical formulation comprises said NSAID compound in an amount which is less than that required to substantially alter the plasma pharmacokinetics of a compound of formula (I) as defined above in a subject to be treated.

The invention further provides a process for the preparation of a pharmaceutical formulation which process comprises bringing into association a combination of a compound of formula (I) as defined above or a pharmaceutically acceptable salt or ester thereof and a NSAID compound with one or more pharmaceutically acceptable carriers therefor in a unit dose in which said NSAID compound is in an amount which is less than that required to substantially alter the plasma pharmacokinetics of the compound of formula (I) in a subject to be treated.

Furthermore, the invention also provides a kit comprising in combination for simultaneous, separate or sequential use in modulating neoplastic growth, a compound of formula (I) as defined above or a pharmaceutically acceptable salt or ester thereof and a NSAID compound, wherein said NSAID is provided in a unit dose comprising an amount of NSAID which is less than that required to substantially alter the plasma pharmacokinetics of the compound of formula (I) in a subject to be treated.

Figure 1:
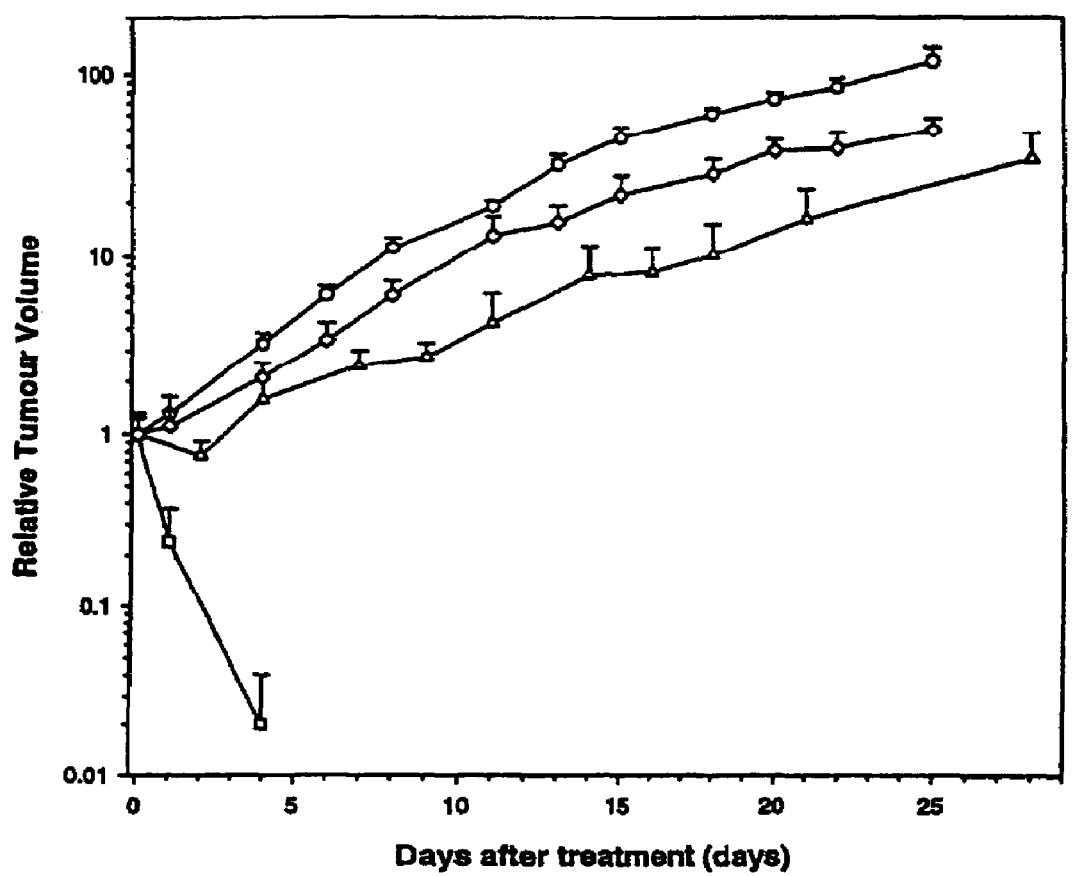
FIG. 1. shows growth of colon 38 tumours untreated (circle), or following treatment with DMXAA (25 mg/kg, triangle), diclofenac (5 mg/kg, diamond) or the combination (DMXAA (25 mg/kg) and diclofenac (5 mg/kg, square). Mean±SEM (standard error of the mean) of 5 mice per group.

In one embodiment the NSAID compound is a cylooxygenase inhibitor. Preferably the NSAID is a COX-2 inhibitor. In preferred embodiments of the invention, the NSAID is selected from the group comprising diclofenac, salicylate, ibuprofen, sulindac celecoxib and rofecoxib. In a particularly preferred embodiment, the NSAID is diclofenac.

The term 'potentiating ratio' is used herein to indicate that the compound of formula (I) as defined above or pharmaceutically acceptable salt or ester thereof and the NSAID compound are present in a ratio such that the antitumour activity of the combination is greater than that of either the compound of formula (I) or the NSAID compound alone or of the additive activity that would be predicted for the combinations based on the activities of the individual components. Thus the individual components act synergistically in combination provided they are present in a potentiating ratio.

The compound of formula (I) as defined above or pharmaceutically acceptable salt or ester thereof and the NSAID compound may be administered simultaneously, separately or sequentially. Preferably the compound of formula (I) as defined above or pharmaceutically acceptable salt or ester thereof and the NSAID compound are administered within 6 hours, more preferably 4 hours, more preferably 2 hours of one another. Most preferably the compound of formula (I) as defined above or pharmaceutically acceptable salt or ester thereof and the NSAID compound are administered simultaneously. For example the two drugs may be administered simultaneously by infusion over 0.2 to 6 hours, for example 0.33 to 3 hours.

Preferably the compound of formula (I) or pharmaceutically acceptable salt or ester thereof and the NSAID compound are administered in a potentiating ratio. Preferably the pharmaceutically acceptable salt is the sodium salt.

A potentiating ratio, for a compound of formula (I) as defined above and the NSAID which may be successfully used to treat cancer, is preferably in the range 150:1 to 1:15, more preferably in the range 75:1 to 1:10, even more preferably 50:1 to 1:5, for example 25:1 to 1:1, 15:1 to 1:1. Suitably, the potentiating ratio is in the range 10:1 to 1:1. Most preferred is a potentiating ratio of approximately 5:1.

As used herein, the term "modulating neoplastic growth" means a change of at least 10% in the rate of neoplastic growth relative to the rate of growth of neoplastic cells in the absence of a compound as described herein. It is preferred that the change be a decrease in neoplastic growth, and further preferred that the change be by at least 20%, 30%, 40%, 50%, 60%, 70%, 80%, 90% or more, up to and including 100%, or cessation of growth. Modulation of neoplastic growth, as the term is used herein also encompasses regression of neoplasm size, mass or cell number relative to pre-treatment levels.

The amount of a combination of a compound of formula (I) or formula (II) as defined above, for example DMXAA or a pharmaceutically acceptable salt or ester thereof and the NSAID compound required to be effective as an anticancer agent will, of course, vary and is ultimately at the discretion of the medical practitioner. The factors to be considered include the route of administration and nature of the formulation, the mammal's bodyweight, age and general condition and the nature and severity of the disease to be treated.

In general, a suitable effective dose of NSAID to be used in combination with DMXAA for administration to man for treatment of cancer may be a dose which is substantially non-toxic to man and which does not substantially affect the pharmacokinetics of DMXAA. A dose of NSAID may be considered to not substantially affect the pharmacokinetics of a compound e.g. DMXAA if, for example, it does not substantially inhibit glucoronidation or 6-methylhydroxylation of that compound, for example it inhibits glucoronidation or 6-methylhydroxylation of that compound by less than 40%, preferably less than 30%, 20%, 15%, 10%, 5%, 2%, most preferably less than 1% or 0.1%.

In general, a suitable effective dose of a combination of DMXAA and an NSAID for administration to man for treatment of cancer is in the range of 600 to 4900 mg/m$^2$ of DMXAA and 0.01 to 5 mg/kg of an NSAID such as diclofenac. For example from 600 to 4900 mg/m$^2$ of DMXAA and 0.025 to 4 mg/kg of an NSAID such as diclofenac, suitably 1200 to 3500 mg/m$^2$ of DMXAA and 0.05 to 4 mg/kg of NSAID, particularly 2000 to 3000 mg/m$^2$ of DMXAA and 0.1 to 3 mg/kg of NSAID, more particularly 2250 to 2750 mg/m$^2$ of DMXAA and 0.2 to 2.5 mg/kg of NSAID, more particularly 2250 to 2750 mg/m$^2$ of DMXAA and 0.05 to 2 mg/kg of NSAID. A particularly preferred dose is in the range 2250 to 2750 mg/m$^2$ of DMXAA and 0.75 to 1.25 mg/kg mg/m$^2$ of NSAID. A further particularly preferred dose is in the range 2250 to 2750 mg/m$^2$ of DMXAA and 0.1 to 0.5 mg/kg of NSAID, for example 0.1 to 0.25 mg/kg.

The compound of formula (I), or pharmaceutically acceptable salt or ester thereof and the NSAID compound may be administered in any suitable form. However, for use according to the present invention the combination of a compound of formula (I) or a pharmaceutically acceptable salt or ester thereof and a NSAID compound is preferably presented as a pharmaceutical formulation.

Pharmaceutical formulations comprise the active ingredients (that is, the combination of compound of formula (I) or a pharmaceutically acceptable salt or ester thereof and a NSAID compound) together with one or more pharmaceutically acceptable carriers therefor and optionally other therapeutic and/or prophylactic ingredients. The carrier(s) must be acceptable in the sense of being compatible with the other ingredients of the formula and not deleterious to the recipient thereof.

Accordingly, the present invention provides a pharmaceutical formulation comprising a combination of compound of formula (I) or a pharmaceutically acceptable salt or ester thereof and a NSAID compound in association with one or more pharmaceutically acceptable carriers therefor, wherein the NSAID compound is present in an amount which is less than that required to substantially alter the plasma pharmacokinetics of compound of formula (I) in a subject to which the combination is administered.

The present invention further provides a process for the preparation of a pharmaceutical formulation which process comprises bringing into association a combination of compound of formula (I) or a pharmaceutically acceptable salt or ester thereof and a NSAID compound with one or more pharmaceutically acceptable carriers therefor, wherein said NSAID compound is present in said pharmaceutical formulation in an amount which is less than that required to substantially alter the plasma pharmacokinetics of compound of formula (I) in a subject to which the pharmaceutical formulation is administered.

Pharmaceutical formulations include those suitable for oral, topical (including dermal, buccal and sublingual), rectal and parenteral (including subcutaneous, intradermal, intramuscular and intravenous) administration as well as administration by naso-gastric tube.

The formulation may, where appropriate, be conveniently presented in discrete dosage units and may be prepared by any of the methods well known in the art of pharmacy. All methods include the step of bringing into association the active ingredients with liquid carriers or finely divided solid carriers or both and then, if necessary, shaping the product into the desired formulation.

Preferably the pharmaceutical formulations are adapted for parenteral administration, most preferably intravenous administration. For example the compounds may be administered intravenously using formulations for each compound already known in the art.

Pharmaceutical formulations suitable for oral administration wherein the carrier is a solid are most preferably presented as unit dose formulations such as boluses, capsules or tablets each containing a predetermined amount of the active ingredients. A tablet may be made by compression or moulding, optionally with one or more accessory ingredients. Compressed tablets may be prepared by compressing in a suitable machine the active compounds in a free-flowing form such as a powder or granules optionally mixed with a binder, lubricant, inert diluent, lubricating agent, surface-active agent or dispersing agent. Moulded tablets may be made by moulding an inert liquid diluent. Tablets may be optionally coated and, if uncoated, may optionally be scored. Capsules may be prepared by filling the active ingredients, either alone or in admixture with one or more accessory ingredients, into the capsule shells and then sealing them in the usual manner. Cachets are analogous to capsules wherein the active ingredients together with any accessory ingredient(s) are sealed in a rice paper envelope. The combination of compound of formula (I) or a pharmaceutically acceptable salt or ester thereof and a NSAID compound may also be formulated as dispersible granules, which may for example be suspended in water before administration, or sprinkled on food. The granules may be packaged e.g. in a sachet. Formulations suitable for oral administration wherein the carrier is a liquid may be presented as a solution or a suspension in an aqueous liquid or a non-aqueous liquid, or as an oil-in-water liquid emulsion.

Formulations for oral administration include controlled release dosage forms e.g. tablets wherein the active ingredients are formulated in an appropriate release—controlling matrix, or are coated with a suitable release—controlling film. Such formulations may be particularly convenient for prophylactic use.

The active ingredients may also be formulated as a solution or suspension suitable for administration via a naso-gastric tube.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in moulds.

Pharmaceutical formulations suitable for parenteral administration include sterile solutions or suspensions of the active combination in aqueous or oleaginous vehicles. Injectible preparations may be adapted for bolus injection or continuous infusion. Such preparations are conveniently presented in unit dose or multi-dose containers which are sealed after introduction of the formulation until required for use. Alternatively, the active ingredients may be in powder form which are constituted with a suitable vehicle, such as sterile, pyrogen-free water, before use.

The combination of compound of formula (I) or a pharmaceutically acceptable salt or ester thereof and NSAID compound may also be formulated as a long-acting depot preparation, which may be administered by intramuscular injection or by implantation e.g. subcutaneously or intramuscularly. Depot preparations may include, for example, suitable polymeric or hydrophobic materials, or ion-exchange resins. Such long-acting formulations are particularly convenient for prophylactic use.

It should be understood that in addition to the aforementioned carrier ingredients the pharmaceutical formulations for the various routes of administration described above may include, as appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Compounds of formula (I) and (II) may be prepared by methods known in the art. For instance, compounds of formula (I), wherein $R_1$, $R_2$, $R_3$, and $R_4$, are as defined in part (b) of the definition of formula (I) as recited above, may be prepared using the methods as disclosed in U.S. Pat. No. 4,602,034 (Briet et al), the contents of which are herein incorporated by reference.

Compounds of formula (III), (IV) and (V) are known and may be prepared using the methods known in the art. For example, compounds of formula (III), (IV) and (V) and their preparation are described in the following references, the contents of which are herein incorporated by reference:

Rewcastle et al, Journal of Medicinal Chemistry 34(1): 217-22, January 1991;

Rewcastle et al, Journal of Medicinal Chemistry 34(2): 491-6, February 1991;

Atwell et al, Journal of Medicinal Chemistry 33(5): 1375-9, May 1990;

Rewcastle et al, Journal of Medicinal Chemistry 34(9): 2864-70, September 1991;

Rewcastle et al, Journal of Medicinal Chemistry 32(4): 793-9, April 1989

DMXAA may be prepared according to the methods described in Rewcastle et al, Journal of Medicinal Chemistry 34(1): 217-22, January 1991, the contents of which are incorporated herein by reference.

The NSAIDs may be prepared by any suitable method known to the skilled person. For example, diclofenac is a well known compound and can be prepared by methods known to those skilled in the art.

The efficacy of treatment as described herein can be determined by one of skill in the art. Treatment is considered effective if neoplastic growth is modulated, as that term is defined herein. Thus, a slowing, halt or regression of neoplastic growth following treatment as described herein is considered effective treatment.

Examples of cancers that may be treated using methods as described herein include, without limitation, acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, polycythemia vera, Hodgkin's disease, non-Hodgkin's disease, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, lelomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, seminoma, embryonal carcinoma, Wilms tumor, cervical cancer, uterine cancers, testicular cancers, lung carcinoma, small cell lung carcinomas, bladder carcinoma, epithelial carcinom, gliomas, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma.

It is to be understood that the present invention covers all combinations of suitable and preferred groups described hereinabove.

The present invention will now be illustrated, but is not intended to be limited, by means of the following examples.

EXAMPLES

Materials and Methods

C57B1/6 mice from the Animal Resource Unit, University of Auckland, were bred and housed under conditions of constant temperature and humidity, with sterile bedding and food, according to institutional ethical guidelines. All mice were aged between 8 and 12 weeks.

Drugs and Drug Administration

DMXAA was synthesized as the sodium salt (Rewcastle et al (1990) Journal of National Cancer Institute 82:528-529). DMXAA sodium salt was dissolved in sterile water and 25 mg/kg in a volume of 0.1 ml per 10 g body weight was injected intraperitoneally (i.p.) into mice.

Diclofenac (Sigma) was dissolved in dimethylsulphoxide, and was injected i.p. into mice in a volume of 25 μl per 10 g body weight. The required dose of diclofenac was injected concurrently with DMXAA.

Tumour Growth Delay Assay

Colon 38 tumour fragments (~1 mm³) were implanted subcutaneously (s.c.) in the left flank of anaesthetized (sodium pentobarbital, 81 mg/kg) mice. The experiments were initiated when tumours were approximately 3-5 mm in diameter. Tumour-bearing mice were treated with drugs according to the administration schedule described before, and the tumours measured using calipers, three times weekly thereafter. Tumour volumes were calculated as $0.52a^2b$, where a and b are the minor and major axes of the tumour, respectively. The arithmetic means were calculated for each time point, counting cured tumours as zero volume. The growth delay was determined as the difference in the number of days required for the control versus treated tumours to increase four times in volume.

Pharmacokinetic Studies

DMXAA Sample Preparation

Mice were treated i.p. with DMXAA or DMXAA combination with diclofenac. At 0.25, 1.5, 3, 4.5 and 6 hours after treatment, the mice were halothane-anaesthetised and the blood was collected through ocular sinus into heparinised plastic microcentrifuge tubes. The animals were then immediately killed by cervical dislocation. Tumour tissues were taken out immediately after mouse being killed, and stored at −70° C. for later DMXAA assay.

Data Analysis and Assay Validation

For DMXAA pharmacokinetic studies, the AUC was calculated as a function of time using the log-trapezoidal rule. Cmax was the maximum concentration measured. The half-life ($T_{1/2}$) was calculated as $0.693/Lz$, where Lz is the slope of the terminal linear-portion of the log-concentration-time curve. The relative recoveries and coefficients of variation (CV) for the intra-assay accuracy and precision were 85-115% and 6-10% (n=8 for plasma assay, and n=10 for tumour/liver assay) respectively, over the concentration range of 0.2-100 μM (for DMXAA assay). Inter-assay accuracy was also acceptable with similar relative recoveries (85-115%) and CVs (6-10%, n=8 for plasma assay, and n=10 for tumour/liver assay).

DMXAA Assay

DMXAA concentrations in plasma and in homogenates of tumour were measured using a specific reverse-phase high-pressure liquid chromatography (HPLC) assay. Automated solid-phase extraction and 2,5-dimethylxanthenone-4-acetic acid (as the internal standard) were used in this assay. Mouse plasma samples were centrifuged (6000 rpm, 5 min) (Biofuge A, Heraeus Christ GmbH, Germany), and then diluted 10-fold with 10 mM ammonium acetate buffer (pH 5.5). Tumour samples were homogenized in 1 ml of 10 mM ammonium acetate buffer (pH 5.5). Thereafter 200 μl of diluted plasma or tumour homogenates were mixed with the internal standard solution (50 μl, 20 μM), and proteins precipitated using ice-cold acetonitrile/methanol (3:1 v/v). After centrifugation (3000 rpm, 10 min, 4° C.), the supernatants were added to ammonium acetate buffer (9 ml) and transferred automatically onto 1 ml/100 mg preconditioned (1 ml acetonitrile/methanol. 3:1 v/v, and 1 ml Milli Q water) C18 Bond-Elut cartridges (Varian, Harbor City, Calif.). This was accomplished using an automated sample preparation with an extraction column system (ASPEC, Gilson Medical, Middleton, Wis.). The cartridges were washed with Milli Q water (1 ml) and the compounds of interest eluted using 1 ml acetonitrile containing 30% methanol.

The elutes were evaporated to dryness using a centrifugal evaporator (Jouan, St. Nazaire, France) and the residues were dissolved in 200 μl mobile phase. Aliquots (18 μl) were automatically injected into the chromatograph (Waters WISP 712B sample injector and Model 510 pump; Water Associates, Milford, Mass.) with a fluorescence detector (Shimadzu Model RF530; Shimadzu, Kyoto, Japan) with excitation and emission wavelengths set at 345 and 409 nm, respectively, and a LUNA 5μ C18(2) 100×4.6 mm stainless steel column (Phenomenex). Integration and data acquisition were achieved using a Unicam 4880 chromatography data system (Unicam, Cambridge, UK). Compounds were eluted from the column (retention time of DMXAA and internal standard were 8 and 6 minutes, respectively) using a mobile phase of 10 mM ammonium acetate buffer (pH 5.0) and acetonitrile (3:1, v/v) at a flow rate of 1.5 ml/min. Human plasma calibration samples were prepared by adding DMXAA to plasma over the concentration range 0.2-100 μM. Human plasma calibration samples were used. The peak-height ratios of DMXAA to the internal standard were plotted against DMXAA concentration in the calibration standards and the best fit straight line obtained by linear regression analysis. Quantitation of DMXAA in mouse plasma samples was achieved by determining the peak-height ratio in mouse plasma samples and using the equation obtained from the calibration curve.

Statistics The statistical significance of tumour growth inhibition was tested by Students' t-test. Volumes of tumours were calculated using the formula 0.52×minor axis squared× major axis.

Example 1

Tumour Growth Delay

DMXAA (25 mg/kg)+diclofenac (5 mg/kg), a combination which was shown to be non-toxic in toxicity experiments in colon 38 tumour-bearing mice (results not shown), was compared with the DMXAA monotherapy against colon 38 tumours implanted s.c. in mice. The tumour growth delay experiment was conducted using 4 drug regimes: untreated controls, DMXAA alone (25 mg/kg), diclofenac alone (5 mg/kg), and a combination group of DMXAA (25 mg/kg)+ diclofenac (5 mg/kg). The results are shown in FIG. 1.

Diclofenac alone was found to have no significant effect on the growth of colon 38 tumours. DMXAA produced a growth delay of ~6 days, but none of the mice were cured. With the combination group, there was a remarkable improvement in the antitumour response in that all the mice were cured (100%). The results showed that coadministration of diclofenac with DMXAA can lead to significant increases in antitumour activity.

Example 2

The Enhanced Antitumour Effect in the Presence Of Diclofenac Cannot Be Attributed to Pharmacokinetic Effects on the Metabolism of DMXAA The effect of diclofenac on DMXAA's plasma concentrations was next examined. The 3 hour time point was determined as being the best time point to use because of less variability (Dr Kestell, personal communication). The only combination that gave a significant increase (56%) in DMXAA plasma concentration, was DMXAA (25 mg/kg)+ diclofenac (100 mg/kg) (Table 1). All the doses of diclofenac below 100 mg/kg had no significant effect on DMXAA plasma concentrations 3 hours after administration.

Figure 2:
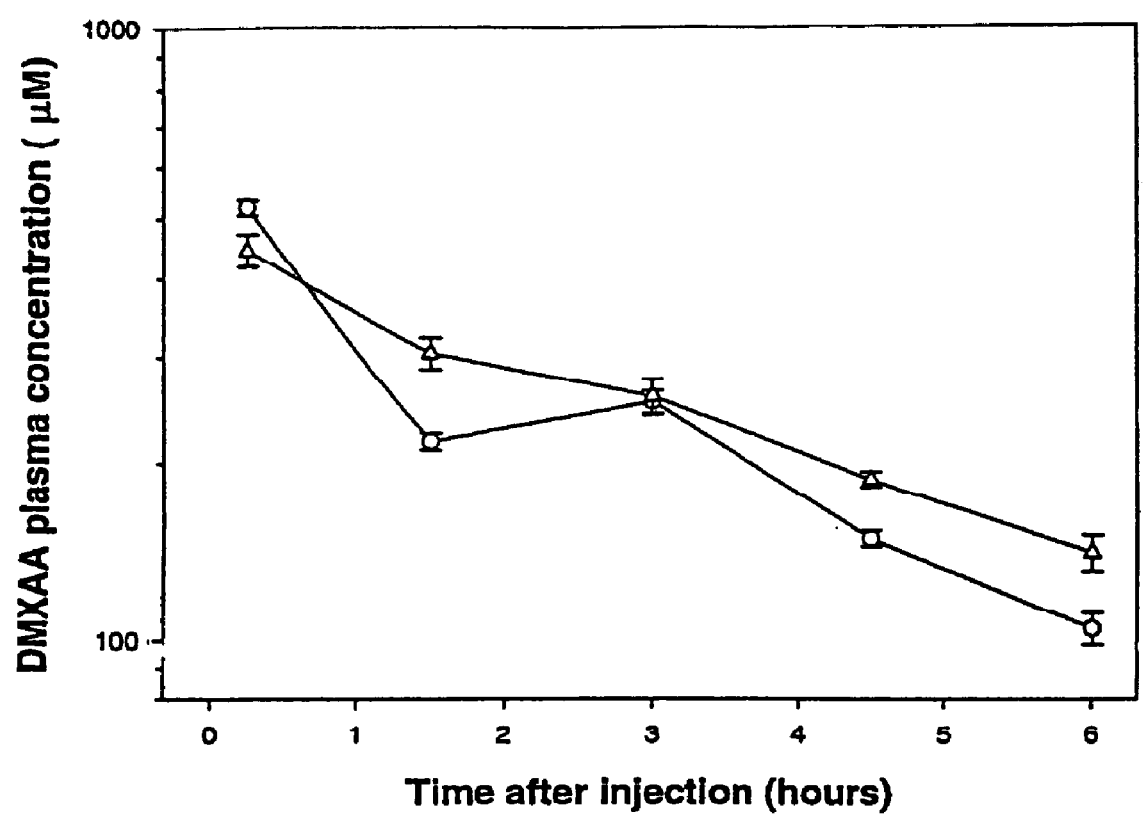
FIG. 2 shows the time course of DMXAA plasma concentration following treatment with DMXAA(25 mg/kg, circle), or the combination (DMXAA (25 mg/kg) and diclofenac (5 mg/kg, triangle). Mean±SEM of 3 mice per time point.

An experiment was carried out to determine if diclofenac at 5 mg/kg had any effect on the plasma pharmacokinetics of DMXAA over the first 6 hours. No statistical difference in the DMXAA plasma concentrations were observed with or without coadministered diclofenac (FIG. 2). The AUC values, 1333 μM·hr and 1514 μM·hr, for DMXAA alone and in combination with diclofenac respectively, were also not statistically different. Similarly, the half-life of DMXAA in plasma (2.7 hours) was not statistically different from that obtained with coadministered diclofenac (3.6 hours). These results suggested that the reason for the observed improved antitumour activity with coadministered diclofenac was not as a result of alterations in the plasma pharmacokinetics of DMXAA.

Example 3

The Effect of Diclofenac on Intratumoral DMXAA

Figure 3:
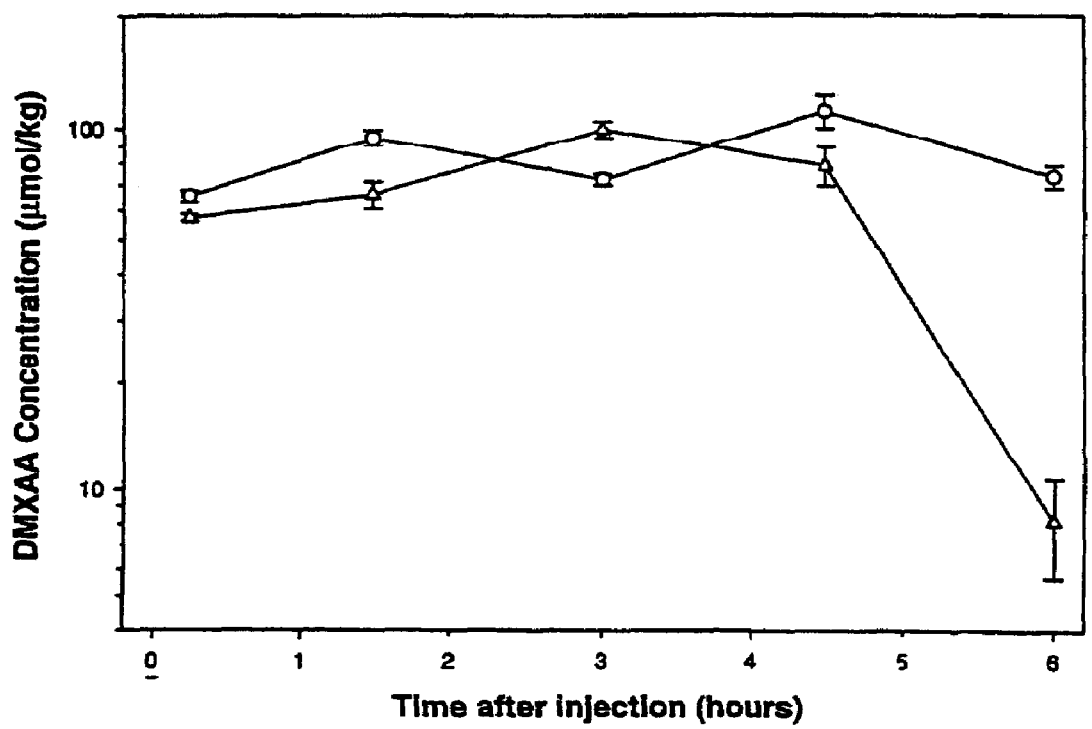
FIG. 3 shows the time course of DMXAA intratumoural concentration following treatment with DMXAA (25 mg/kg, circle), or the combination (DMXAA (25 mg/kg) and diclofenac (5 mg/kg, triangle). Mean±SEM of 3 mice per time point.

There was no significant difference in the DMXAA concentration in colon 38 tumours following treatment with DMXAA alone or in combination with diclofenac over a five hour time course (FIG. 3). At six hours, however, there was a significant reduction in the DMXAA concentration. The AUC values, 507 μM·hr and 388 μM·hr, of DMXAA monotherapy and combination therapy respectively, showed no significant difference. The Cmax values, 111 μM and 100 μM, of DMXAA monotherapy and combination therapy respectively, similarly showed no significant difference. These results further indicate that the improved anti tumour activity in the presence of diclofenac is not attributable to altered pharmacokinetics of DMXAA.

Discussion

Diclofenac at high concentrations has been shown in vitro to inhibit glucuronidation (>70%) and 6-methylhydroxylation (>54%) of DMXAA (Zhou et al, Cancer Chemother. Pharmacol., 47: 319-326). In vivo diclofenac (100 mg/kg) is able to increase the plasma concentration and AUC of DMXAA by 24-31% in mice (Zhou et al, Cancer Chemother. Pharmacol., 47: 319-326). Diclofenac (100 mg/kg) increased DMXAA plasma concentration by 56% (Table 5), but lower doses had no significant effect.

In this study, it had been shown that NSAIDS, in particular diclofenac at 5 mg/kg could enhance DMXAA anti tumour activity (FIG. 1). The growth delay for DMXAA monotherapy was around 6 days with no cure, whereas for DMXAA combination therapy, there was a significant increase in the number of cures. These results suggest that by coadministration of diclofenac, the anti tumour activity of DMXAA can be increased.

The time-course experiments (0-6 hours) of plasma and intratumoral concentrations in both DMXAA monotherapy and combination therapy were conducted (FIG. 2 and FIG. 3). Both of Cmax and AUC values induced by both treatments were similar. In this study, diclofenac was used at 5 mg/kg, a concentration significantly below the effective concentration that can inhibit glucuronidation of DMXAA. These results therefore suggest that the anti tumour activity enhanced by the dose combination of DMXAA (25 mg/kg)+diclofenac (5 mg/kg) was not due to the direct alteration in the pharmacokinetics of DMXAA.

Although there was no significant difference between two therapies in intratumoral AUC values, but there was a significant decrease at the 6 hour time point (FIG. 3), where the intratumoral concentration of DMXAA in the combination group was much lower than the one in the monotherapy. Without being bound by any one theory, it is possible that this might result from diclofenac enhancing DMXAA anti tumour activity by increasing the rate of reduction in tumor blood flow to the tumour, reducing the concentration of DMXAA inside the tumour tissue.

All publications mentioned in this specification are herein incorporated by reference. Various modifications and variations of the described methods and materials of the invention will be apparent to those skilled in the art without departing from the scope and spirit of the invention. Although the invention has been described in connection with specific preferred embodiments, it should be understood that the invention as claimed should not be unduly limited to such embodiments. Indeed various modifications of the described modes for carrying out the invention which are obvious to those skilled in the art are intended to be within the scope of the following claims.

The invention claimed is:

1. A method for treating colon cancer, which comprises administering to a mammal in need of treatment an effective amount of 5,6-dimethylxanthenone-4-acetic acid (DMXAA) or a pharmaceutically acceptable salt thereof and concomitantly or sequentially administering an effective amount of diclofenac, wherein said effective amount of said diclofenac is in the range of 0.01 to 5 mg/kg, and wherein the ratio of said DMXAA to said diclofenac is in the range of 150:1 to 1:1.

2. The method of claim 1 wherein the ratio of DMXAA: diclofenac is in the range 10:1 to 1:1.

3. The method of claim 1 wherein the ratio of DMXAA: diclofenac is about 5:1.

4. The method of claim 1 wherein said DMXAA or the pharmaceutically acceptable salt thereof and said diclofenac are administered concomitantly.

5. The method of claim 1 wherein the said DMXAA or the pharmaceutically acceptable salt thereof and said diclofenac are administered sequentially.

6. The method according to claim 1, wherein said mammal is a human.

* * * * *

UNITED STATES PATENT AND TRADEMARK OFFICE
CERTIFICATE OF CORRECTION

PATENT NO.        : 7,462,642 B2                                  Page 1 of 1
APPLICATION NO.   : 10/946833
DATED             : December 9, 2008
INVENTOR(S)       : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 579 days.

Signed and Sealed this

Twenty-sixth Day of October, 2010

David J. Kappos
*Director of the United States Patent and Trademark Office*